United States Patent [19]

DeLuca et al.

[11] 4,196,133

[45] Apr. 1, 1980

[54] 24,24-DIFLUORO-25-HYDROXYCHOLECALCIFEROL

[75] Inventors: Hector F. DeLuca, Madison, Wis.; Nobuo Ikekawa, Tokyo, Japan; Yoko Tanaka, Madison, Wis.; Yoshiro Kobayashi, Tokyo, Japan

[73] Assignee: Wisconsin Alumni Research Foundation, Madison, Wis.

[21] Appl. No.: 17,168

[22] Filed: Mar. 5, 1979

[51] Int. Cl.$^2$ .................................................. C07J 9/00
[52] U.S. Cl. .................................................. 260/397.2
[58] Field of Search .................................. 260/397.2

[56] References Cited

U.S. PATENT DOCUMENTS

| | | | |
|---|---|---|---|
| 3,993,675 | 1/1976 | Uskokovic et al. | 260/397.2 |
| 4,069,321 | 1/1978 | Jones et al. | 260/397.2 |

Primary Examiner—Elbert L. Roberts
Attorney, Agent, or Firm—Howard W. Bremer

[57] ABSTRACT

The invention provides a new derivative of vitamin $D_3$, 24,24-difluoro-25-hydroxycholecalciferol.

The compound is characterized by vitamin D-like activity in its ability to increase intestinal calcium transport, increase serum calcium and inorganic phosphorous concentration and to prevent the development of rickets. It would find ready application as a substitute for vitamin $D_3$ and in the treatment of disease states evincing calcium-phosphorous imbalance and which are non-responsive to vitamin $D_3$ therapy.

3 Claims, No Drawings

24,24-DIFLUORO-25-HYDROXYCHOLECALCIFEROL

The invention described herein was made in the course of work under a grant or award from the Department of Health, Education, and Welfare.

DESCRIPTION

1. Technical Field

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective vitamin $D_3$ must be converted in vivo to its hydroxylated forms. For example, the vitamin is first hydroxylated in the liver to form 25-hydroxy vitamin $D_3$ and is further hydroxylated in the kidney to produce $1\alpha,25$-dihydroxy vitamin $D_3$ or 24,25-dihydroxy vitamin $D_3$. The $1\alpha$-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

2. Background Art

References to various of vitamin D derivatives are extant in the patent and other literature. See, for example, U.S. Pat. Nos. 3,565,924 directed to 25-hydroxycholecalciferol; 3,697,559 directed to 1,25-dihydroxycholecalciferol; 3,741,996 directed to $1\alpha$-hydroxycholecalciferol; 3,907,843 directed to $1\alpha$-hydroxyergocalciferol; 3,715,374 directed to 24,25-dihydroxycholecalciferol; 3,739,001 directed to 25,26-dihydroxycholecalciferol; 3,786,062 directed to 22-dehydro-25-hydroxycholecalciferol; 3,847,955 directed to 1,24,25-trihydroxycholecalciferol; 3,906,014 directed to 3-deoxy-$1\alpha$-hydroxycholecalciferol; 4,069,321 directed to the preparation of various side chain flourinated vitamin $D_3$ derivatives and side chain fluorinated dihydrotachysterol$_3$ analogs.

DISCLOSURE OF INVENTION

A new derivative of vitamin $D_3$ has now been found which expresses excellent vitamin D-like activity and which, therefore, could serve as a substitute for vitamin $D_3$ in its various known applications and would be useful in the treatment of various diseases such as osteomalacia, osteodystrophy and hypoparathyroidism.

This derivative has been identified as 24,24-difluoro-25-hydroxycholecalciferol (24,24-difluoro-25-hydroxy vitamin $D_3$ or 24 $F_2$,25-OHD$_3$).

BEST MODE FOR CARRYING OUT THE INVENTION

The compound of this invention was synthesized in accordance with the following description and abbreviated schematic:

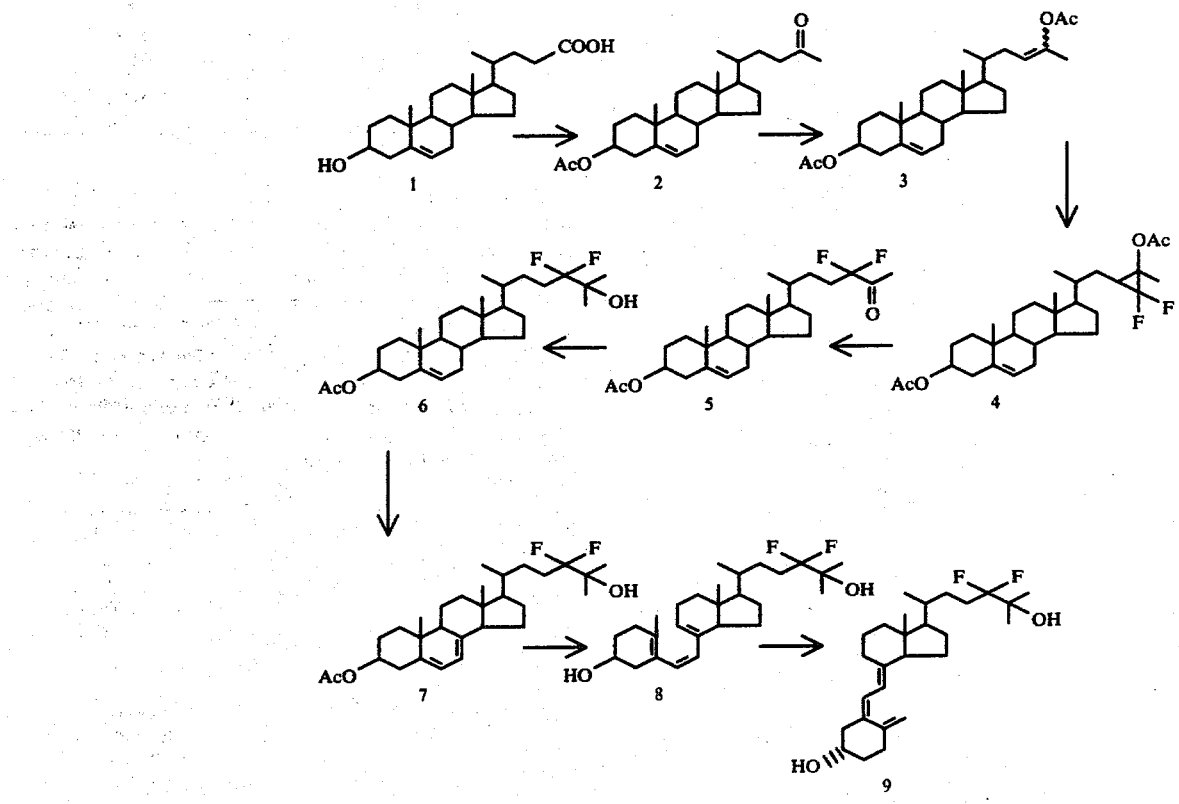

Cholenic acid 1 was treated with dihydropyran in a suitable organic solvent ($CH_2Cl_2$) at 0° in the presence of P-toluene sulfonic acid and then with 1 N Na OH in ethanol at 20° to form the cholenic acid tetrahydropyranyl ether (protection of the hydroxyl group in the A ring). This compound was then treated with an excess of CH$_3$Li in tetrahydrofuran (THF)-ethyl ether at 0° C. for four hours after which the protective tetrahydropyranyl group was removed by treatment with p-TsOH in CH$_2$Cl$_2$-methanol for 24 hours at 20° C. Subsequent acetylation (Ac$_2$O-pyridine-CH$_2$,20°, 24 hours) gave the methylketone 2 (mp 148°–151°, δ2.12 (3H,s,C-25), m/e 354 (M-60)) (Yield=6% overall from 1).

The methylketone 2 was refluxed for seven hours in acetic anhydride in the presence of p-TsOH (enolacetylation) to give the diacetate 3 (mp 109°–110°, δ5.02 (1H, m, C-23) 1.90 (3H,s,C-25) m/e 396 (M-60)). The diacetate was then converted to the difluorocyclopropane 4 by heating with sodium chlorodifluoro-acetate in diglyme at 170° for 0.5 hours. Yield, 34%; mp 112°–115°, 5.38 (1H,m,C-6), 4.60 (1H,m,C-3), 2.05 (3H,s,24-OAc), 2.02 (3H,s, 3-OAc), 1.60 (3H,m,C-26), m/e 446 (M-60)).

Treatment of 4 with LiOH in THF-methanol-water at 20° C. for two hours followed by acetylation (AC$_2$O-pyridine-CH$_2$Cl$_2$,20°, 24 hr.) gave, after chromatography on silica gel, the difluoroketone 5(9.3% yield, mp 135°–136-5°, δ2.26 (3H,t,J$_{HF}$ =1 Hz,C-26), m/e 404 (M-60)). The difluoroketone was obtained in a mixture with the 23(E)-and the 23(Z)-conjugated ketone, with the difluoroketone being separated by chromatography on silica gel).

The difluoroketone 5 was reacted with an excess of CH$_3$Mg1 in ethyl ether at 0° C. for 15 minutes and was then acetaylated (AC$_2$O-pyridine-CH$_2$Cl$_2$, 20°, 20 hr.) to furnish the 25-carbinol, 6, in 85% yield (mp 163°–164-5°, δ1.28 (6H,s,C-26,27), m/e 420 (M-60)). The carbinol, 6, was allylically brominated by reacting it with N-bromo-succinimide in refluxing CCl$_4$ for 25 minutes. The brominated compound was then dehydrobrominated by treatment with s-collidine in refluxing xylene for 15 minutes to give a mixture of the 4,6-diene and the 5,7-diene, 7. The 5,7-diene (λmax 263, 272, 282 and 292 nm, m/e 419 (M-59)) was isolated in 28% yield, by treatment with pTsOH in acetone at 20° for 15 hours followed by preparative thin-layer chromatography (benzene-ethyl acetate (15:1), 3times). The recovered 5,7-diene was saponified by treatment with 5% KOH-methanol at 20° C. for 15 hours and then irradiated (Hanovia high pressure quartz mercury vapor lamp, model 654A36; 200 W) in a mixture of ethanol and benzene for 2.5 minutes at b 0° C. to give the previtamin 8 in solution. The irradiated solution was refluxed for one hour and then fractionated with thin-layer chromatography (silicagel, benzene-ethyl acetate, (5.1), 3 times) and high pressure liquid chromatography (Zorbax SIL, 25 cm×2.1 mm i.d., available through the DuPont Co., Wilmington, Delaware) CH$_2$Cl$_2$) to yield 24,24-difluoro-25-hydroxy vitamin D$_3$, 9, (λmax 264 nm, λmin 228 nm, m/e 436 (M+), 421, 418, 403, 377, 271, 253, 136, 118).

Statement

If it is desired for certain purposes the acetylated 5,7-diene after recovery as described above can be saponified by well known means (5% KOH in MeOH, 20°, 15 hours) to convert the acetoxy group at the 3-position to hydroxyl.

Also, if desired, the previtamin 8 can be recovered by evaporation of solvent at 5° and the subsequent chromatograph on silica gel, and subsequently converted to the vitamin.

Biological Activity

Male weanling rats were housed in hanging wire cages and fed ad libitum the low calcium, vitamin D deficient diet described by Suda et al (J. Nutr. 100, 1049 (1970)) for three weeks prior to their use in the following assays.

Intestinal Calcium Transport

Groups of five or six rats fed as above were given respectively a single dose (650 pmole) of either 24,24-difluoro-25-hydroxy vitamin D$_3$ (24 F$_2$,25-OH$_2$) or 25-hydroxy vitamin D$_3$ (25-OHD$_3$) dissolved in 0.05 ml of 95% ethanol intrajugularly 8, 23 or 30 hours prior to sacrifice. The rats in the control group were given the ethanol vehicle only. They were then killed by decapitation after the respective times prescribed and their duodena were used to measure the intestinal calcium transport activity in accordance with the techniques of Martin and DeLuca (Am. J. Physiology 216, 1351 (1969)). Results are shown in the table below.

Table 1

| Compound Given | $^{45}$Ca serosal/$^{45}$Ca mucosal | | |
|---|---|---|---|
| | 8 h | 23 h | 30 h |
| Control | 2.7 ± 0.2*(a) | 2.5 + 0.4(a) | 2.6 ± 0.2(a) |
| 24F$_2$,25-OHD$_3$ | 6.6 ± 1.2(b) | 5.9 ± 0.6(b) | 8.2 ± 2.1(b) |
| 25-OHD$_3$ | 5.0 ± 0.7(c) | 5.5 ± 0.8(c) | 5.7 ± 1.4(c) |
| Significance of difference | (b) & (c) from (a) $p<0.001$ (b) from (c) $p<0.025$ | (b) & (c) from (a) $p<0.001$ (b) from (c) N.S. | (b) & (c) from (a) $p<0.001$ (b) from (c) $p<0.05$ |

*Standard deviation of the mean

To show the effect of small doses of 24F$_2$,25-OHD$_3$ on intestinal calcium transport rats fed the low calcium diet as indicated above, in groups of 5 or 6 were given a single dose of 24F$_2$,25-OHD$_3$ or 25-OHD$_3$ dissolved in 0.05 ml of 95% ethanol intrajugularly. Rats in the control group received the vehicle alone. Either 20 hours or 168 hours after receiving the dose the rats were killed and their duodena were used to measure the intestinal calcium transport activity in accordance with the Martin and DeLuca procedure referenced above. Results are shown in Table 2 below.

Table 2

| Compound Given | Dosage (pmole/rat) | $^{45}$Ca serosal/$^{45}$Ca mucosal | |
|---|---|---|---|
| | | 20 h | 168 h |
| Control | | 1.5 ± 0.5*(a) | 2.0 ± 0.4(a) |
| 24F$_2$, 25-OHD$_3$ | 6.5 | 1.9 ± 0.6(b) | 2.1 ± 0.1(b) |
| | 32.5 | 1.9 ± 0.3(b) | 3.7 ± 0.9(c) |
| 25-OHD$_3$ | 6.5 | 1.8 ± 0.4(b) | 2.1 ± 0.2(b) |
| | 32.5 | 2.2 ± 0.6(b) | 3.8 ± 0.7(d) |
| Significance of difference | | (b) from (a) N.S. | (b) from (a) N.S. (c) from (a) $p<0.05$ (d) from (a) $p<0.001$ |

*Standard derivative of the mean

Serum Calcium Concentration

Rats fed as indicated above were divided into groups of six rats each. The rats in one group were given a single dose of 650 p mole of 24F$_2$,25-ODH$_3$, in the second group a dose of 650 p mole of 25-OHD$_3$ (in each case the vitamin $D_3$ derivative was dissolved in 0.05 ml of 95% ethanol) while the third group (control) was given the vehicle alone. The materials were administered intrajugularly either 8 or 29 hours prior to sacrifice.

The rats were killed by decapitation after the indicated times, the blood collected and centrifuged to obtain the serum. The serum (0.1 ml) was mixed with 1.9 ml of 0.1% NaCC solution and the calcium concentration was measured with an atomic absorption spectraphotometer (Perkin-Elmer Model HO-214). Results are shown in the table below.

Table 3

| Compound Given | Serum calcium (mg/100 ml) | |
|---|---|---|
| | 8 h | 24 h |
| Control | 7.7 ± 0.2*[a] | 3.9 ± 0.1[a] |
| 24F$_2$,25-OHD$_3$ | 4.9 ± 0.2[b] | 5.2 ± 0.2[b] |
| 25-OHD$_3$ | 4.7 ± 0.3[b] | 5.3 ± 0.2[b] |
| Significance of difference | (b) from (a) $p<0.001$ | (b) from (a) $p<0.001$ |

*Standard derivative of the mean

Antirachitic Activity

Male weanling rats (Holtzman Co., Madison, Wisconsin) maintained in hanging wire cages were fed, in groups of six the low phosphorous diet described in Am. J. Physiol 204, 833 (1963) (Guroff, DeLuca and Steenbock) and were simultaneously given either 24F$_2$, 25-OHD$_3$ dissolved in 0.1 ml ethanol/propylene glycol (5/95, v/v) subcutaneously every day for two weeks. Rats in the control group were fed in like manner but received only the vehicle subcutaneously.

Twenty-four hours after receiving the last subcutaneous dose the rats were killed by decapitation and their duodena were used for measurement of intestinal calcium transport as described above. Their radii and ulnae were removed for measurement of widened epiphyseal plates, and femurs for determination of ash content (femurs were dried to constant weight and then ashed in a muffle furnace at 650° C. for 8 hours.)

Results obtained are shown in the table below.

Table 4

| Compound Given | Dosage (pmole) | Intestinal Calcium Transport (I/O) | Width of Epiphyseal Plate (mm) | Femur Ash | |
|---|---|---|---|---|---|
| | | | | Total (mg) | Percent |
| Control | | 2.1 ± 0.3*[a] | 3.2 ± 0.3[a] | 29.71 ± 3.06[a] | 27.3 ± 2 |
| 24F$_2$,25-OHD$_3$ | 6.5 | 5.7 ± 1.2[b] | 1.5 ± 0.2[b] | 37.53 ± 3.82[b] | 30.9 ± 1.1 |
| | 6.5 | 11.2 ± 2.3[c] | 0.5 ± 0.1[c] | 52.95 ±3.55[c] | 38.5 ± 1.1 |
| 25-OHD$_3$ | 6.5 | 5.4 ± 0.3[d] | 1.5 ± 0.3[d] | 39.83 ± 6.31[d] | 31.7 ± 2 |
| | 6.5 | 10.8 ± 2.0 [e] | 0.6 ± 0.2[e] | 53.66 ± 6.72[e] | 38.4± 2.7 |
| *Significance of difference | | (b),(c),(d), & (e) from (a) $p<0.001$ | (b) from (a) $p<0.005$ (d) from (a) $p<0.025$ (c) & (e) from (a) $p<0.001$ | (b) from (a) $p<0.005$ (d) from (a) $p<0.025$ (c) & (e) from (a) $p<0.001$ | (b) from $p<0.01$ (d) from $p<0.025$ (c) & (e) from (a) $p<0.00$ |

*Standard derivation of the mean

Male weanling rats were fed the low phosphorous diet referenced above and then divided into groups of five or six rats each. The rats in each group were given respectively a single dose (as shown in the table below) of either 24F$_2$,25-OHD$_3$ or 25-OHD$_3$ dissolved in 0.05 ml of 95% ethanol intrajugularly. Rats in the control group received the ethanol vehicle above. 168 hours after receiving the indicated dosage the rats were killed by decapitation, the blood of each group was collected and the radii and ulnae were removed to determine antirachitic activity in accordance with the rat line test (U.S. Pharmacopoeia, 15th Rev., Mack Publishing Co., Easton, Pa., 1955, p. 889). The blood was centrifuged immediately after collection to yield the serum. The inorganic phosphorous in the serum was determined by the method of Chen et al (Anal. Chem., 28, 1756, (1956)).

Results obtained are shown in the table below.

Table 5

| Compound Given | Dosage (pmole) | Serum Inorganic Phosphorous (mg/100 ml) | Line Test Score (Unit) |
|---|---|---|---|
| Control | | 1.6 ± 0.2*[a] | 0 |
| 24F$_2$,25-OHD$_3$ | 130 | 3.0 ± 0.2[b] | 4.4 ± 1.4[a] |
| | 325 | 3.5 ± 0.4[b] | 5 |
| 25-OHD$_3$ | 130 | 3.3 ± 0.1[b] | 2.6 ± 0.6[b] |
| | 325 | 3.6 ± 0.4[b] | 3.5 ± 0.6 |
| Significance of difference | | (b) from (a) $p<0.001$ | (b) from (a) $p<0.025$ |

*Standard deviation of the mean

To determine the antirachitic activity in response to a daily dose of 24F$_2$,25-OHD$_3$ rats were fed the low phosphorous diet referenced above for three weeks. They were then given either 24F$_2$,25-OHD$_3$ or 25-OHD$_3$ (in each case, 65 $p$ mole dissolved in 0.1 ml ethanol/propylene glycol (5/95, v/v) subcutaneously every day for 8 days while being maintained on the same diet (9 rats were in each group). The rats in the control group (4 rats) were given only the ethanol/propylene glycol vehicle in the same manner.

Twenty-four hours after receiving the last dose they were killed and their radii and ulnae were removed and used for measuring antirachitic activity (rat line test, supra) while the femurs were removed and ashed as described above.

Results obtained are shown in the table below.

Table 6

| Compound Given | Line Test Score (Unit) | Total Femur Ash (mg) | Percent Ash (%) |
|---|---|---|---|
| Control | 0 | 23.80 ± 3.98*[a] | 19.5 ± 3.4[a] |
| 24F$_2$,25-OHD$_3$ | >>5 | 37.03 ± 4.94[b] | 26.2 ± 1.8[b] |
| 25-OHD$_3$ | >>5 | 38.56 ± 5.79[b] | 27.4 ± 2.4[b] |
| Significance of difference | | (b) from (a) $p<0.001$ | (b) from (a) $p<0.005$ |

*Standard deviation of the mean

It is evident from the foregoing data that 24,24-difluoro-25-hydroxy vitamin $D_3$ exhibits pronounced vitamin D-like activity and appears to be wholly as effective in this regard as 25-hydroxy vitamin D₃ (see U.S. Pat. No. 3,565,924).
We claim:
1. 24,24-difluoro-25-hydroxy vitamin D₃.
2. 24,24-difluoro-25-hydroxy previtamin D₃.
3. Compounds having the formula
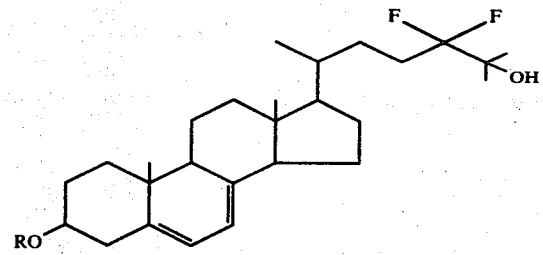
where R is hydrogen or acetyl.
* * * * *